United States Patent
Kubo et al.

(10) Patent No.: US 10,181,187 B2
(45) Date of Patent: Jan. 15, 2019

(54) INFORMATION PROCESSING APPARATUS, METHOD THEREOF, INFORMATION PROCESSING SYSTEM, AND COMPUTER-READABLE STORAGE MEDIUM THAT DISPLAY A MEDICAL IMAGE WITH COMMENT INFORMATION

(71) Applicant: CANON KABUSHIKI KAISHA, Tokyo (JP)

(72) Inventors: Takeshi Kubo, Kyoto (JP); Gakuto Aoyama, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 105 days.

(21) Appl. No.: 15/249,881

(22) Filed: Aug. 29, 2016

(65) Prior Publication Data

US 2017/0069084 A1  Mar. 9, 2017

(30) Foreign Application Priority Data

Sep. 9, 2015 (JP) ................................ 2015-177914
Apr. 13, 2016 (JP) ................................ 2016-080480

(51) Int. Cl.
| | | |
|---|---|---|
| *G06T 7/00* | (2017.01) | |
| *G06K 9/46* | (2006.01) | |
| *G06K 9/62* | (2006.01) | |
| *H04N 5/232* | (2006.01) | |
| *G06K 9/00* | (2006.01) | |
| *G06T 11/60* | (2006.01) | |

(Continued)

(52) U.S. Cl.
CPC ............ *G06T 7/0012* (2013.01); *A61B 5/743* (2013.01); *A61B 6/5294* (2013.01);
(Continued)

(58) Field of Classification Search
CPC ..................... G06T 7/0012; G06T 7/70; G06T 2207/20101; G06T 2207/20104;
(Continued)

(56) References Cited

U.S. PATENT DOCUMENTS

| | | | |
|---|---|---|---|
| 8,625,867 B2 | 1/2014 | Moriya | ........................ 382/128 |
| 9,342,145 B2 | 5/2016 | Moffett | .................. G06F 3/013 |

(Continued)

FOREIGN PATENT DOCUMENTS

| | | |
|---|---|---|
| CN | 103941855 A | 7/2014 |
| CN | 104281683 A | 1/2015 |

(Continued)

OTHER PUBLICATIONS

Office Action dated Jun. 15, 2018, issued in corresponding Chinese Patent Application No. 201610807491.X.

*Primary Examiner* — Andrew W Johns
(74) *Attorney, Agent, or Firm* — Venable LLP

(57) ABSTRACT

An information processing apparatus includes a report acquisition unit adapted to acquire report information including a region of interest in a medical image and comment information associated with the region of interest, a related region acquisition unit adapted to acquire a region related to the region of interest in the medical image, a determination unit adapted to determine a display position of a display region of the comment information so as not to make the display region of the comment information overlap the related region, and a display control unit adapted to display the medical image including the comment information so that the comment information is displayed at the determined display position of the display region on a display unit.

28 Claims, 12 Drawing Sheets

(51) Int. Cl.
  *A61B 5/00* (2006.01)
  *A61B 6/00* (2006.01)
  *A61B 5/055* (2006.01)
(52) U.S. Cl.
  CPC ....... *G06K 9/00442* (2013.01); *G06K 9/4671* (2013.01); *G06K 9/6267* (2013.01); *G06T 7/004* (2013.01); *G06T 7/0081* (2013.01); *G06T 11/60* (2013.01); *H04N 5/232* (2013.01); *A61B 5/055* (2013.01); *G06K 2009/4666* (2013.01); *G06T 2207/20112* (2013.01); *G06T 2207/20224* (2013.01)
(58) Field of Classification Search
  CPC . G06T 2207/20108; G06T 2207/20212; G06T 2207/20221; G09G 2340/0464; G09G 2340/10; G09G 2340/12; G09G 2340/14; G09G 2380/08; G06F 19/32; G06F 19/321; G16H 30/00; G16H 30/40
  See application file for complete search history.

(56) References Cited

U.S. PATENT DOCUMENTS

| | | | |
|---|---|---|---|
| 2005/0107690 A1 | 5/2005 | Soejima | 600/425 |
| 2010/0135562 A1* | 6/2010 | Greenberg et al. | 382/131 |
| 2013/0249903 A1* | 9/2013 | Isokawa et al. | G06T 7/0012 345/419 |
| 2014/0306992 A1* | 10/2014 | Tsujimoto et al. | G06T 11/60 345/632 |
| 2015/0205917 A1 | 7/2015 | Mabotuwana et al. | G06F 19/321 |
| 2017/0091949 A1* | 3/2017 | Akasaka et al. | G06T 7/0081 |

FOREIGN PATENT DOCUMENTS

| | | |
|---|---|---|
| CN | 104584018 A | 4/2015 |
| JP | 2006-255021 A | 9/2006 |
| JP | 2011-083590 A | 4/2011 |
| WO | 2011/033769 A1 | 3/2011 |

\* cited by examiner

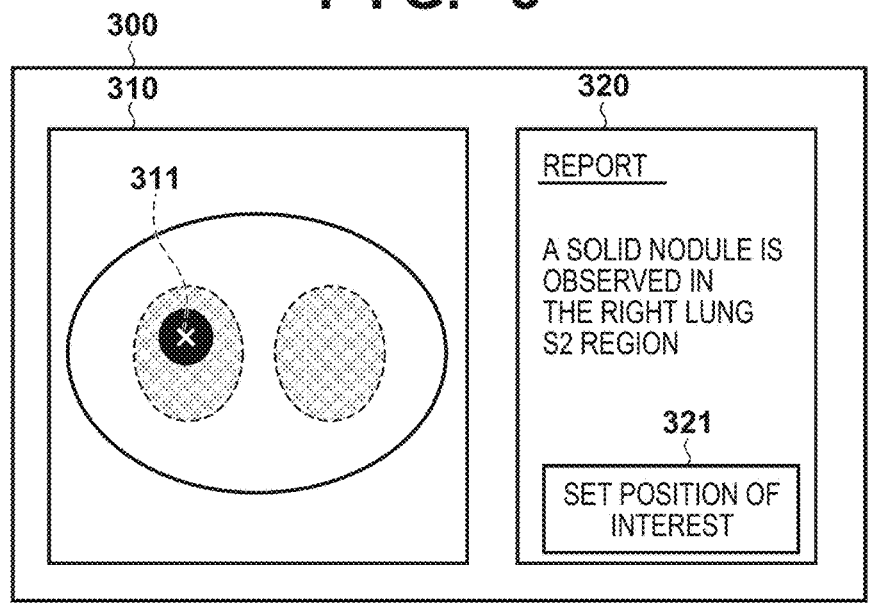
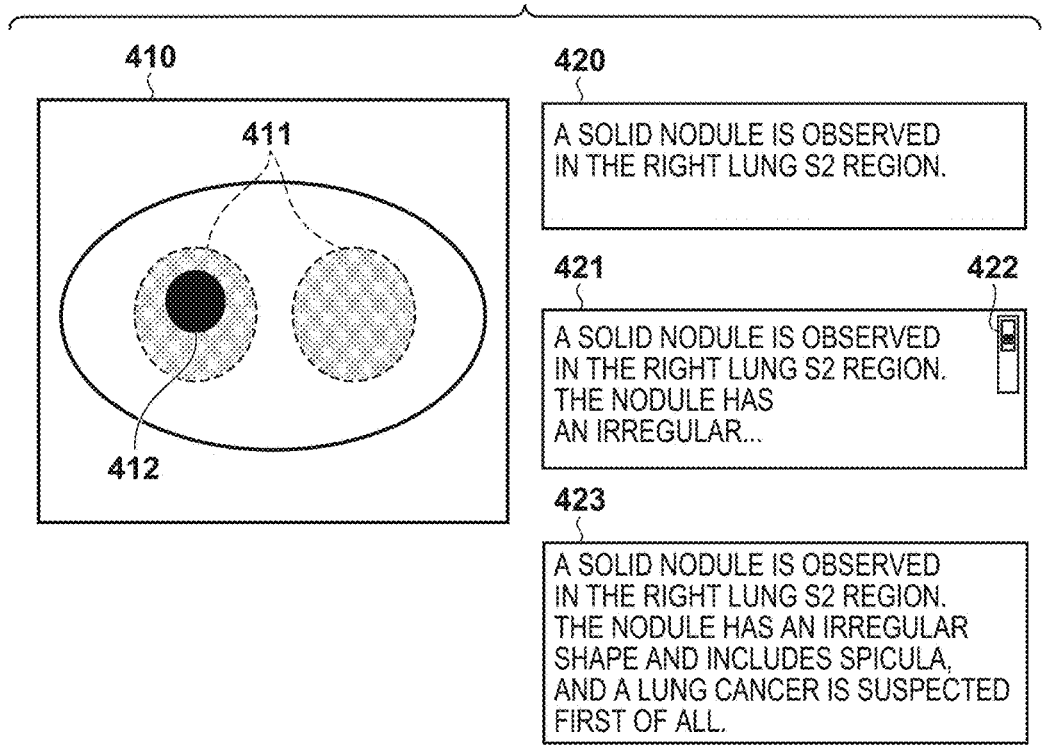

| KEYWORD | ACQUIRED REGION | | |
|---|---|---|---|
| BRAIN | CEREBRUM | CEREBELLUM | — |
| LUNG | RIGHT LUNG FIELD | LEFT LUNG FIELD | BRONCHUS |
| HEART | HEART | AORTA | POSTCAVAL VEIN |
| HEPATIC ORGAN | LIVER | GALLBLADDER | — |
| STOMACH | GULLET | STOMACH | DUODENUM |
| MAMMA | BREAST | GREATER PECTORAL MUSCLE | — |

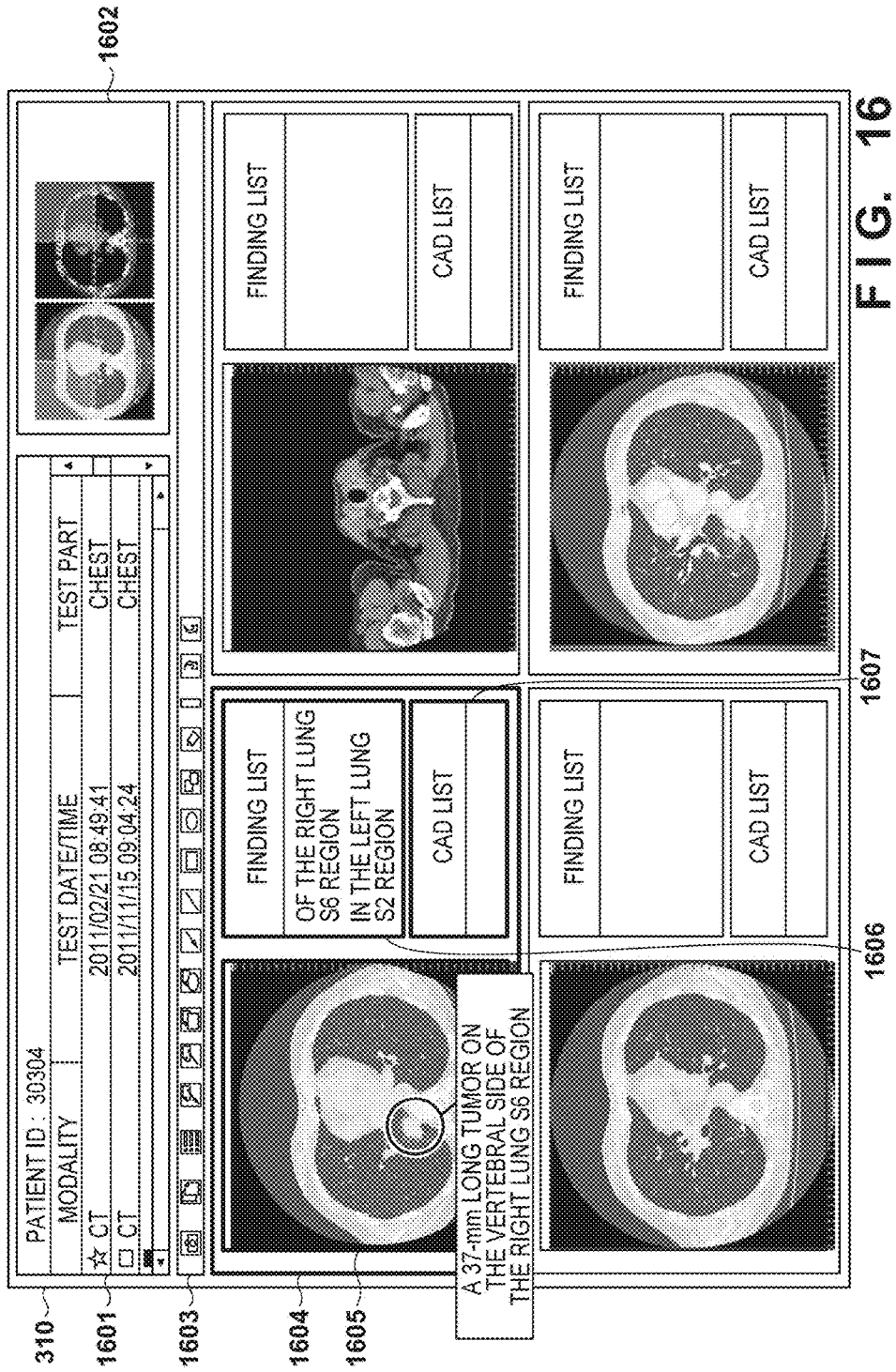

INFORMATION PROCESSING APPARATUS, METHOD THEREOF, INFORMATION PROCESSING SYSTEM, AND COMPUTER-READABLE STORAGE MEDIUM THAT DISPLAY A MEDICAL IMAGE WITH COMMENT INFORMATION

BACKGROUND OF THE INVENTION

Field of the Invention

The present invention relates to an information processing apparatus, a method thereof, an information processing system, and a computer-readable storage medium and, more particularly, to a medical image display technique.

Description of the Related Art

On a medical scene, imaging of a patient is performed using a medical imaging apparatus such as an X-ray CT (computed tomography) apparatus, an MRI (nuclear magnetic resonance imaging) apparatus, or a PET (positron emission tomography) apparatus. CT is short for Computed Tomography, MRI is short for Magnetic Resonance Imaging, and PET is short for Positron Emission Tomography. Medical images are created by performing various kinds of image processing for image data obtained by imaging and saved in a data server in the hospital for a predetermined period. As for the image diagnosis operation of a doctor, a target medical image is searched for using a medical image display apparatus (also called a viewer) and displayed on a monitor, and the image diagnosis is conducted using various functions of the medical image display apparatus. The doctor records the result of the image diagnosis as an interpretation report.

When referring to the recorded interpretation report, the user refers to it while associating the medical image with the description contents of the interpretation report. However, it is sometimes difficult to easily specify a position on the medical image represented by the description contents of the interpretation report. In addition, the user needs a time to refer to the interpretation report while associating the two pieces of information, that is, the medical image and the interpretation report with each other.

Japanese Patent Laid-Open No. 2011-083590 describes displaying, on a medical image, the information of a morbid portion described in an interpretation report. According to this arrangement, a character string in an interpretation report is linked with a position on a medical image indicated by the character string, and the character string is displayed near the position. Hence, the user can correctly grasp the position on the medical image indicated by the character string described in the interpretation report and correctly refer to the interpretation report without taking a time.

In the arrangement of Japanese Patent Laid-Open No. 2011-083590, however, the position of the character string displayed on the medical image is determined without considering the anatomical structure or the contents of the interpretation report. For this reason, the character string is sometimes overlaid at an anatomically important position on the medical image or at a position on the medical image related to the contents of the interpretation report. In this case, the user can hardly confirm the anatomical structure or the contents of the interpretation report on the medical image.

SUMMARY OF THE INVENTION

The present invention has been made in consideration of the above problems, and provides a technique capable of more easily grasping the correspondence between a medical image and an interpretation report.

According to one aspect, the present invention provides an information processing apparatus that includes a report acquisition unit adapted to acquire report information including a region of interest in a medical image and comment information associated with the region of interest, a related region acquisition unit adapted to acquire a region related to the region of interest in the medical image, a determination unit adapted to determine a display position of a display region of the comment information so as not to make the display region of the comment information overlap the related region, and a display control unit adapted to display the medical image including the comment information so that the comment information is displayed at the determined display position of the display region on a display unit.

According to another aspect, the present invention provides an information processing apparatus that includes a report acquisition unit adapted to acquire report information including a region of interest in a medical image and comment information associated with the region of interest, a related region acquisition unit adapted to acquire a related region in the medical image based on a character string included in the comment information, a determination unit adapted to determine a display position of a display region of the comment information so as not to make the display region of the comment information overlap the related region, and a display control unit adapted to display the medical image including the comment information so that the comment information is displayed at the determined display position of the display region on a display unit.

According to still another aspect, the present invention provides an information processing system that includes a report acquisition unit adapted to acquire report information including a region of interest in a medical image and comment information associated with the region of interest, a related region acquisition unit adapted to acquire a region related to the region of interest in the medical image, a determination unit adapted to determine a display position of a display region of the comment information so as not to make the display region of the comment information overlap the related region, and a display control unit adapted to display the medical image including the comment information so that the comment information is displayed at the determined display position of the display region on a display unit.

According to yet another aspect, the present invention provides an information processing system that includes a report acquisition unit adapted to acquire report information including a region of interest in a medical image and comment information associated with the region of interest, a related region acquisition unit adapted to acquire a related region in the medical image based on a character string included in the comment information, a determination unit adapted to determine a display position of a display region of the comment information so as not to make the display region of the comment information overlap the related region, and a display control unit adapted to display the medical image including the comment information so that the comment information is displayed at the determined display position of the display region on a display unit.

According to still yet another aspect the present invention provides an information processing method that includes acquiring, by a report acquisition unit, report information including a region of interest in a medical image and comment information associated with the region of interest, acquiring, by a related region acquisition unit, a region related to the region of interest in the medical image, determining, by a determination unit, a display position of a display region of the comment information so as not to make the display region of the comment information overlap the related region, and displaying, by a display control unit, the medical image including the comment information so that the comment information is displayed at the determined display position of the display region on a display unit.

According to yet still another aspect the present invention, provides an information processing method that includes acquiring, by a report acquisition unit, report information including a region of interest in a medical image and comment information associated with the region of interest, acquiring, by a related region acquisition unit, a related region in the medical image based on a character string included in the comment information, determining, by a determination unit, a display position of a display region of the comment information so as not to make the display region of the comment information overlap the related region; and displaying, by a display control unit, the medical image including the comment information so that the comment information is displayed at the determined display position of the display region on a display unit.

Further features of the present invention will become apparent from the following description of exemplary embodiments (with reference to the attached drawings).

BRIEF DESCRIPTION OF THE DRAWINGS

FIG. 3 is a view showing an example of an interpretation report creation screen;

FIG. 4 is a view showing examples of a medical image and a character string display region;

FIG. 16 is a view showing a detailed display example of an image display region.

DESCRIPTION OF THE EMBODIMENTS

An embodiment of the present invention will now be described with reference to the accompanying drawings. However, the scope of the present invention is not limited to the following arrangement example.

(Medical Image System)

Figure 1:
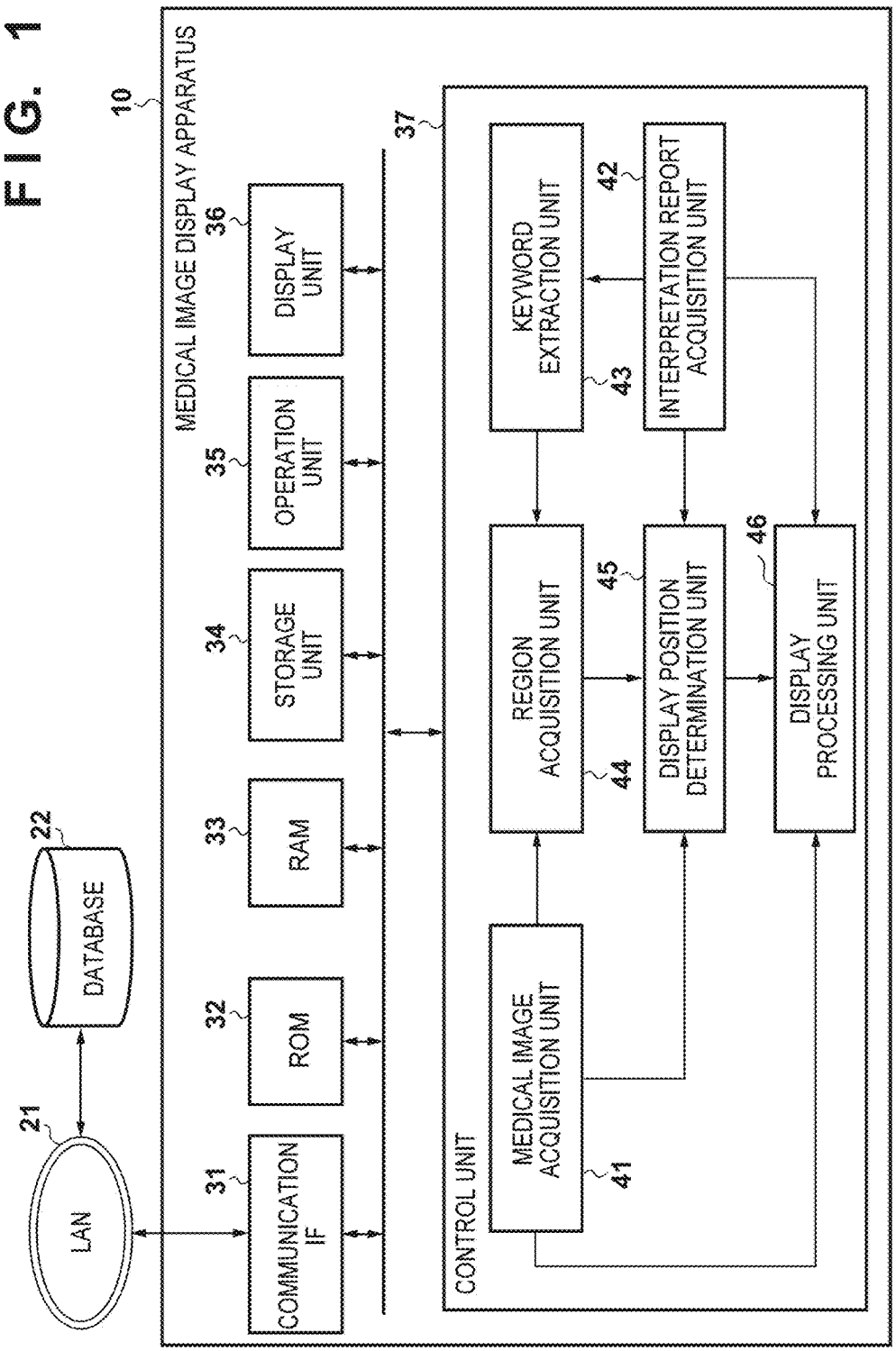
FIG. 1 is a block diagram showing the arrangement of a medical image system.

FIG. 1 is a block diagram showing the overall arrangement of a medical image system (medical image display system) including a medical image display apparatus according to an embodiment of the present invention. The medical image system as an information processing system includes a medical image display apparatus 10 and a database 22. These apparatuses are connected via a communication apparatus so as to be communicable with each other. In this embodiment, an example in which the communication apparatus is formed by a LAN (Local Area Network) 21 will be described. However, the communication apparatus may be formed by a wireless communication apparatus (for example, a wireless LAN) or a public communication network.

The database 22 manages test information such as medical images and interpretation reports. The database 22 holds a medical image and an interpretation report in association. The medical image display apparatus 10 acquires via the LAN 21 a medical image or an interpretation report managed by the database 22.

The medical image display apparatus 10 as an information processing apparatus includes, as its functional components, a communication IF (interface) 31, a ROM (Read Only Memory) 32, a RAM (Random Access Memory) 33, a storage unit 34, an operation unit 35, a display unit 36, and a control unit 37. The communication IF 31 is implemented by, for example, a LAN card, and controls communication between an external apparatus (for example, the database 22) and the medical image display apparatus 10 via the LAN 21. The ROM 32 is a read only memory implemented by a nonvolatile memory or the like, and stores various kinds of programs and the like. The RAM 33 is a writable memory implemented by a volatile memory or the like, and temporarily stores various kinds of information. The storage unit 34 is a storage device implemented by, for example, an HDD (Hard Disk Drive), and stores various kinds of information. The operation unit 35 is implemented by, for example, a keyboard or a pointing device, and inputs a user instruction to the apparatus. The display unit 36 is implemented by, for example, a display, and displays various kinds of information to the user (for example, a doctor). The control unit 37 is implemented by, for example, a CPU (Central Processing Unit), and generally controls the processing of the medical image display apparatus 10.

The control unit 37 includes, as its functional components, a medical image acquisition unit 41, an interpretation report acquisition unit 42, a keyword extraction unit 43, a region acquisition unit 44, a display position determination unit 45, and a display processing unit 46. The medical image acquisition unit 41 acquires a medical image of a patient concerned from the database 22 via the communication IF 31 and the LAN 21 in accordance with a user operation input by the operation unit 35. The medical image acquisition unit 41 outputs the medical image to the region acquisition unit 44, the display position determination unit 45, and the display processing unit 46.

The interpretation report acquisition unit 42 acquires an interpretation report (report information) from the database 22 via the communication IF 31 and the LAN 21 in accordance with a user operation input by the operation unit 35. Note that the interpretation report is the interpretation report corresponding to the medical image acquired by the medical image acquisition unit 41, and a detailed method of creating the interpretation report will be described later. In addition, the report information is information including a region of interest in a medical image of an object (for example, patient) and comment information associated with the region of interest. The report information is a subset of information included in the interpretation report or the interpretation report itself. The interpretation report includes not only an interpretation report registered in an interpretation report server by an interpretation doctor but also an interpretation report before registration or under editing which is input to an interpretation report editing screen. In this case, the above-described report information is information included in the interpretation report under editing, which is information including a region of interest in a medical image of an object and comment information associated with the region of interest.

A part or the whole of the acquired interpretation report is output to the keyword extraction unit 43, the display position determination unit 45, and the display processing unit 46.

The keyword extraction unit 43 performs processing to be described later for the interpretation report acquired by the interpretation report acquisition unit 42, thereby extracting a keyword. The keyword extraction unit 43 outputs the extracted keyword to the region acquisition unit 44.

The region acquisition unit 44 serving as related region acquisition unit performs image processing to be described later for the medical image acquired by the medical image acquisition unit 41 based on the keyword acquired by the keyword extraction unit 43, thereby acquiring an anatomical region in the medical image. The region acquisition unit 44 outputs the acquired anatomical region to the display position determination unit 45.

The display position determination unit 45 determines a display position to display a character string in the interpretation report acquired by the interpretation report acquisition unit 42 on the medical image acquired by the medical image acquisition unit 41. The character string in the interpretation report here indicates a part or the whole of a text described in the interpretation report. Note that the display position is determined by processing to be described later based on the medical image, the interpretation report, and a part or the whole of the region acquired by the region acquisition unit 44. The display position determination unit 45 outputs the determined display position to the display processing unit 46.

The display processing unit 46 displays the medical image acquired by the medical image acquisition unit 41 on the display unit 36 while overlaying the character string in the interpretation report acquired by the interpretation report acquisition unit 42 on the display position determined by the display position determination unit 45.

Note that at least some of the units provided in the control unit 37 may be implemented as independent devices. Alternatively, each unit may be implemented as software (computer program) to implement the function. In this case, the software to implement the function may operate on a server via a network such as a cloud. In this embodiment, an example in which each unit is implemented by software in a local environment will be described.

(Processing Procedure)

The overall processing procedure of the control unit 37 according to this embodiment will be described next with reference to FIGS. 2 to 4. For example, a medical image created by capturing the chest region of an object by an X-ray CT apparatus will be described below as a target. However, the target medical image is not limited to this.

Figure 2:
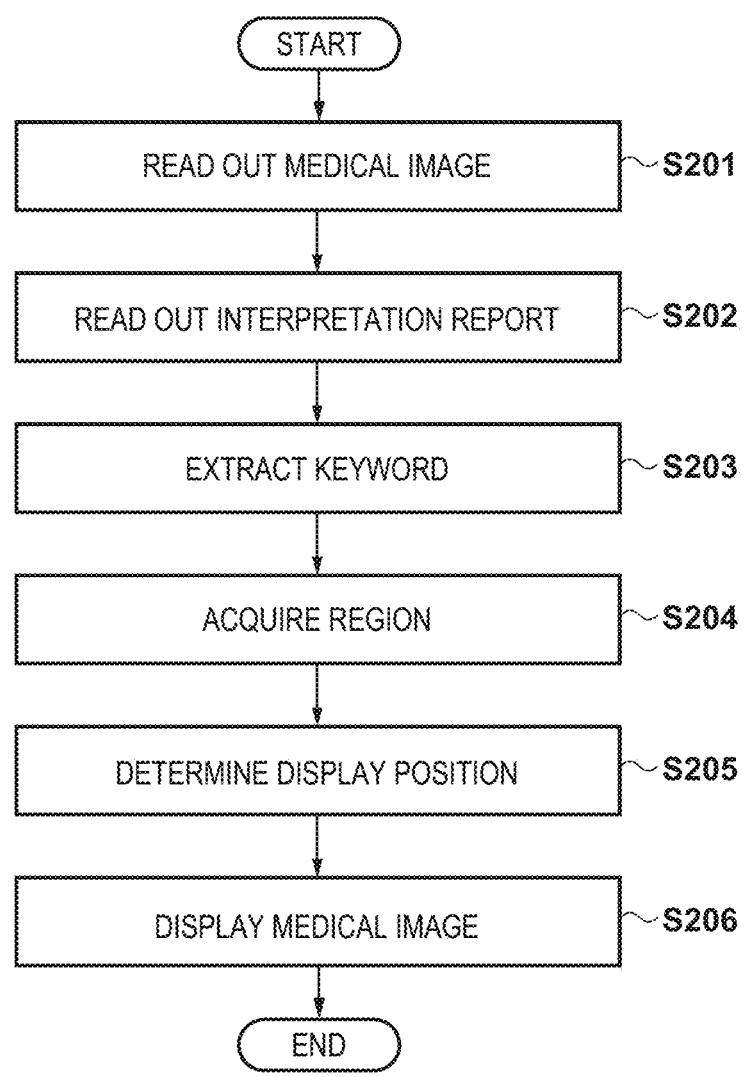
FIG. 2 is a flowchart for explaining the processing procedure of the medical image system.

FIG. 2 is a flowchart of processing performed by the control unit 37. In step S201, the medical image acquisition unit 41 reads out a medical image from the database 22 via the communication IF 31 and the LAN 21 in accordance with a user operation input by the operation unit 35.

In step S202, the interpretation report acquisition unit 42 acquires an interpretation report corresponding to the medical image read out in step S201 from the database 22 via the communication IF 31 and the LAN 21. In this embodiment, the interpretation report is created and registered in the database 22 in the following way.

FIG. 3 shows an interpretation report creation screen 300 as an example of an interpretation report creation screen. An image display region 310 shown in FIG. 3 represents a screen region to display a medical image. Note that various functions of the medical image viewer, such as an enlargement/reduction function for a whole image, an intensity value conversion function, a display position translation function, a graphic drawing function, and an intensity value measuring function are usable for the medical image displayed in the image display region 310. A report display region 320 is a screen region to describe a result of medical image interpretation by the user as a text. The text that describes the interpretation result will be referred to as an interpretation text (comment information) hereinafter. In FIG. 3, "a solid nodule is observed in the right lung S2 region" is described as an interpretation text in the report display region 320. A button 321 is a position-of-interest setting button. A position (to be referred to as a position of interest hereinafter) on the medical image on which the user focuses attention when describing the interpretation text can be set by selecting the button 321. A symbol 311 indicated by x shows the position of interest set by the user. Note that the position of interest may be a pixel or voxel in the image, or may be a region including a plurality of pixels or voxels. The position or region set by the user will be referred to as a region of interest hereinafter. Note that when the user sets a position of interest by an operation input, the information of the set position of interest and the information of a region related to a morbid portion corresponding to the position of interest may be managed by the medical image system as the information of a region of interest.

An example of the interpretation report creation method will be described in detail. The user reads out a medical image to be interpreted from the database 22, and displays it in the image display region 310. The user observes the medical image in detail using various functions of the medical image viewer as described above. The user describes the observation result in the report display region 320 as an interpretation text. In FIG. 3, the interpretation text is described as a free text. However, it may be a structured text. The user then selects the button 321 to set the position of interest for the interpretation text. The position of interest is set using the operation unit 35 (not shown). For example, the user sets the position of interest by clicking it using a pointing device. The position-of-interest setting method is not limited to this, as a matter of course, and any method is usable as long as it can specify position information (to be referred to as position-of-interest information hereinafter) representing the position of interest. The position-of-interest information includes, for example, coordinate values in the medical image. In FIG. 3, the symbol 311 is drawn on the set position of interest. However, recording the position-of-interest information in the medical image display apparatus 10 suffices, and the symbol indicating the position of interest need not always be drawn. The medical image display apparatus 10 saves the interpretation text and the position-of-interest information (or region-of-interest information) in the database 22 in association. Hence, in step S202, the interpretation text and the position-of-interest information are read out as the interpretation report.

In step S203, the keyword extraction unit 43 extracts a keyword set in advance from the interpretation text read out in step S202 by keyword matching. In this embodiment, the keyword is a character string representing anatomical information such as an organ name displayed in the medical image. Examples are cerebrum, cerebellum, eyeball, nose, tooth, lung, bronchus, heart, liver, spleen, pancreas, stomach, large bowel, small bowel, jejunum, ileum, rectum, prostate, uterus, forearm, upper arm, thigh, lower thigh, breast, muscle, bone, spine, sacred bone, coccyx, and pelvis. The organ names described here are merely examples, as a matter of course, and the present invention is not limited to this. The keyword is not limited to an organ name and may be any character string if it can specify a position in a medical image. An example in which "a solid nodule is observed in the right lung S2 region" is described as the interpretation text of an interpretation report, as shown in FIG. 3, will be described below. In this case, "lung" is extracted as a keyword. Alternatively, "right lung" or "right lung S2" capable of more strictly specifying a position in the medical image may be set and extracted. Note that the keyword is extracted here by keyword matching, but may be extracted using another method such as known natural language processing.

In step S204, the region acquisition unit 44 extracts an anatomical region corresponding to the keyword extracted in step S203 from the medical image acquired in step S201, and acquires the region as a region related to the region of interest. A case in which "lung" is extracted as the keyword in step S203 will be described as an example. In this example, the region acquisition unit 44 acquires lung regions from the medical image. More specifically, noise removal is performed from the medical image acquired in step S201 using a smoothing filter. Next, binarization processing is performed using a predetermined threshold (for example, HU value: −200) for the pixel values of the medical image, thereby separating the medical image into an internal region and an external region. The separated internal region is separated into lung regions and other regions using another threshold (for example, HU value: −500), thereby extracting and acquiring lung regions. Note that the anatomical region extraction processing need only extract a predetermined region from the readout medical image, and is not limited to this method. For example, the anatomical region may be extracted using another organ segmentation processing such as a graph cut method.

In step S205, the display position determination unit 45 determines a display position to overlay-display, on the medical image read out in step S201, a part or the whole of the character string that constructs the interpretation text read out in step S202. In this embodiment, the display region is determined so as not to make the display region of the interpretation text overlap the anatomical region. The display position determination method will be described with reference to FIGS. 4, 5A, 5B, 5C, and 5D. A medical image 410 shown in FIG. 4 represents the medical image read out in step S201. In this example, the medical image is an axial (horizontal) image captured by a chest X-ray CT apparatus, and the slice position is the position to which the position of interest is set in step S202. The image at the slice position will be referred to as a slice image of interest hereinafter. Broken lines 411 indicate the boundary lines between the lung fields and the outside in the medical image 410. A symbol 412 represents a morbid portion (nodule). A character string display region 420 represents a region (to be referred to as a character string display region hereinafter) to display some or all of character strings (to be referred to as display character strings hereinafter) of the interpretation text (comment information) read out in step S202. In this embodiment, the character string display region 420 has a predetermined size and shape. In this case, if there are many display character strings relative to the character string display region, it may be impossible to display all the display character strings in the character string display region. In such a case, the display character strings may be scrolled using a scroll bar 422, as indicated by a character string display region 421. The font of the display character strings may be changed to display all display character strings in the character string display region, as indicated by a character string display region 423. Alternatively, a character string that cannot be displayed in the character string display region out of the display character strings may be hidden, or a summary of the display character strings may automatically be generated using known natural language processing and displayed A case in which the character string display region 420 is overlay-displayed on the medical image 410 will be described below. Note that an example in which "lung" is extracted as the keyword of the interpretation text in step S203, and the lung regions in the medical image 410 are acquired in step S204 will be explained.

Figure 5A:
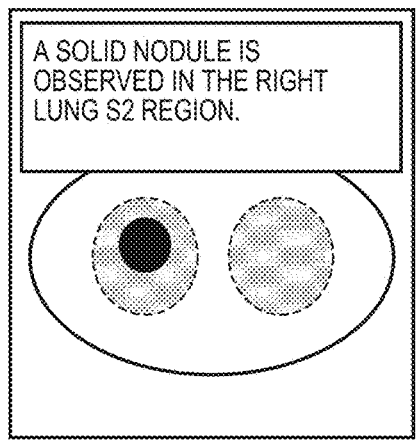
FIGS. 5A, 5B, 5C, and 5D are views showing examples of a character string display region overlay-displayed on a medical image.
Figure 5B:
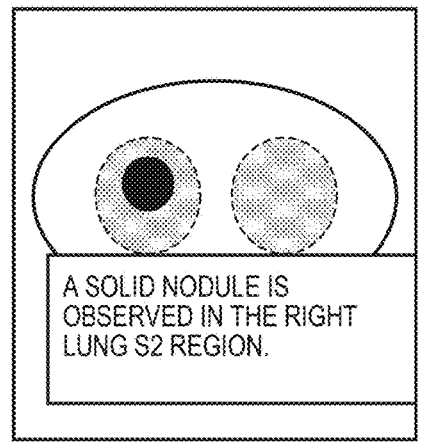
Figure 5C:
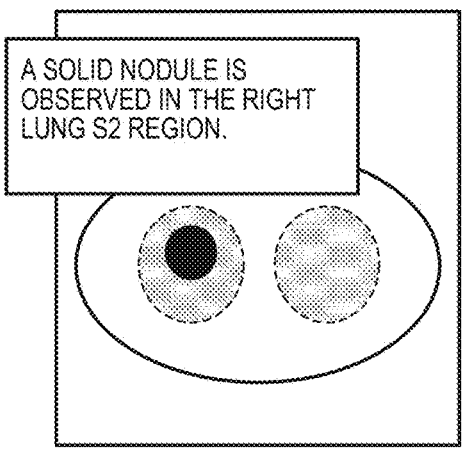
Figure 5D:
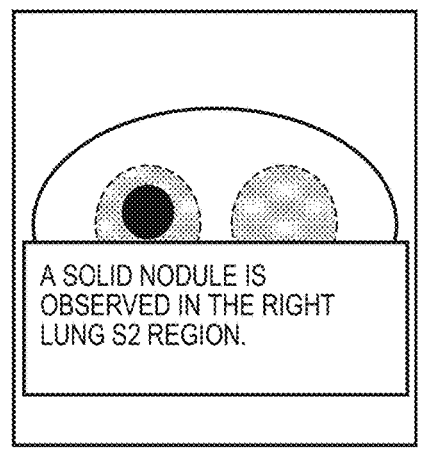

The display position determination unit 45 determines the display position of the character string display region 420 based on predetermined conditions (to be referred to as display position determination conditions hereafter). A description will be made giving an example of display position determination conditions "the entire character string display region is located inside the medical image" and "the character string display region does not overlap the inside of the region extracted based on the keyword of the interpretation text". In this case, the display position of the character string display region 420 is determined to be a region inside the medical image 410 and outside of the broken lines 411. FIGS. 5A, 5B, 5C, and 5D show examples of the display position. In FIGS. 5A and 5B, the display position of the character string display region 420 is located inside the medical image 410 and outside the broken lines 411. Hence, the display positions of the character string display region shown in FIGS. 5A and 5B are appropriate display positions that meet the conditions. In FIG. 5C, the display position of the character string display region 420 is located outside the broken lines 411 but partially located outside of the medical image 410. Hence, the display position of the character string display region shown in FIG. 5C is an inappropriate display position that does not meet the conditions. In FIG. 5D, the display position of the character string display region 420 is located inside the medical image 410 and inside the broken lines 411. Hence, the display position of the character string display region shown in FIG. 5D is an inappropriate display position that does not meet the conditions.

Figure 6:
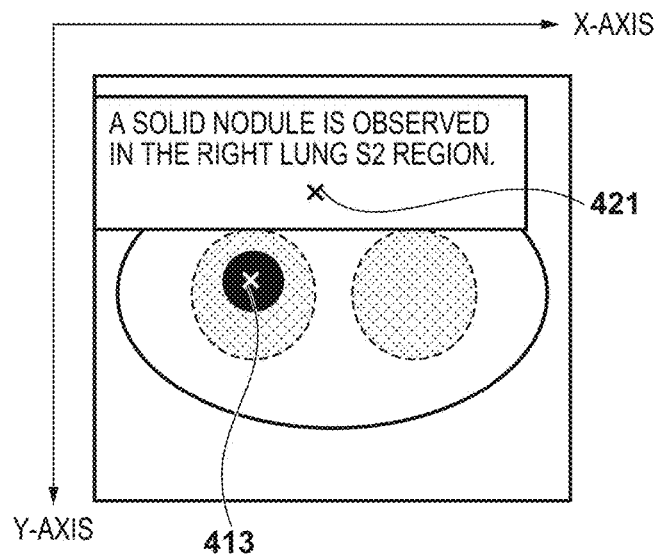
FIG. 6 is a view for explaining an example in which the display position of a character string display region is uniquely determined.

The display position of the character string display region cannot uniquely be determined only by the above-described two display position determination conditions. Hence, in this above-described example, the display position of the character string display region can be any position on the medical image that meets the above-described display position determination conditions. To uniquely determine the display position of the character string display region, a display position determination condition such as "the distance between the position of interest and the center of the character string display region becomes shortest" is additionally set. FIG. 6 shows an example in which the medical image 410 and the character string display region 420 are used. The distance between a position 413 of interest acquired in step S202 and a center 421 of the character string display region 420 is calculated. The character string display region 420 is displayed at such a position that makes the distance between the centers shortest while meeting the other display position determination conditions.

In step S206, the display processing unit 46 overlays the character string display region including some or all of the character strings of the interpretation text acquired in step S202 at the display position determined in step S205 on the medical image acquired in step S201. The display processing unit 46 performs display control to display, on the display unit 36, the medical image with the character string display region including the interpretation text being overlaid.

As described above, according to the medical image display apparatus 10 of this embodiment, the following effects can be obtained. That is, when overlay-displaying some or all of the character strings of the interpretation text on the medical image, the display position is determined in accordance with the contents of the interpretation text. It is therefore possible to avoid the character string from being overlay-displayed on a region of the medical image closely related to the contents of the interpretation text. For this reason, even when viewing the medical image with the character string being overlaid, the user is not hindered from confirming the contents of the character string and is allowed to more easily grasp the correspondence between the medical image and the interpretation report.

If a user other than the interpreter refers to the interpretation report and the medical image in a conference system or the like, it is generally difficult for the user other than the interpreter to understand the contents of the interpretation report. In this case as well, when the interpretation text of the interpretation report is displayed together with the medical image at a position not to overlap the region related to the region of interest, the user other than the interpreter can more easily grasp the correspondence between the medical image and the interpretation report. In this embodiment, since the display position of the character string display region is determined in the region occupied by the medical image, the interpretation text is displayed near the corresponding region of the medical image, and the relationship between the interpretation text and the corresponding region of the medical image can easily be recognized.

Note that, in this embodiment, consideration is made not to cause the character string display region of the interpretation text (comment information) to overlap the region related to the region of interest. An example in which the anatomical region, including the region of interest is acquired, as the region related to the region of interest, has been described. However, the related region is not limited to this. That is, the related region can be an arbitrary partial region of a region occupied by the object in the medical image, which may be referred to when browsing the interpretation text. For example, when an interpretation text is created for a right lung disease, not only the region occupied by the right lung field, but also, other organs (for example, the left lung field and the bronchus) that can be related to the disease may be taken into consideration when determining the display position of the interpretation text. For a disease such as a cancer that may metastasize, a region to which the disease existing in the region of interest may metastasize may be acquired as the related region. Alternatively, a range of a predetermined distance (for example, 10 cm) from the position of interest may be acquired as the related region.

In addition, according to a modification of the interpretation text (comment information), the display position determination unit 45 may change the display position of the character string display region of the interpretation text, and the display processing unit 46 may display, on the display unit 36, the medical image with the modified interpretation text being overlaid at the changed display position. When the display position of the character string display region of the interpretation text on the medical image is changed in accordance with the modification of the interpretation text, the user can always easily grasp the correspondence between the interpretation text and the region of the medical image corresponding to the interpretation text.

According to extraction of the keyword from the character string included in the interpretation text by the region acquisition unit 44, the display processing unit 46 may display a portion corresponding to the keyword out of the character string so as to be distinguished from another character string. For example, the portion corresponding to the keyword may be displayed using a character color or background color different from that of another portion. The portion may be underlined, displayed using a different font, or highlighted. This allows the user to recognize the keyword included in the interpretation text at a glance and easily grasp the contents of the interpretation text.

In this embodiment, an example in which the display position of the character string display region of the interpretation text is determined based on the keyword of the character string included in the interpretation text has been described. However, the display position of the character string display region of the interpretation text need not always be determined based on the keyword as long as the character string display region of the interpretation text does not overlap the related region of the region of interest. For example, the display position of the character string display region of the interpretation text may be determined by acquiring an anatomical region as the related region based on the position of the region of interest in the medical image. Alternatively, if the anatomical region cannot be acquired based on the character string as in a case in which the interpretation text does not include the keyword, the anatomical region may be acquired based on the position of the region of interest in the medical image. The interpretation text can thus be displayed so as not to overlap the anatomical region to be referred to together with the interpretation text at a high possibility without using the keyword, and the correspondence between the medical image and the interpretation report can more easily be grasped.

The image file of the medical image including the interpretation text and display position information representing the display position of the character string display region determined by the display position determination unit 45 may be created. Accordingly, even an apparatus that does not have the function of the medical image display apparatus 10 according to this embodiment can read out the image file and output it to the display to display the relationship between the interpretation text and the corresponding region as long as the apparatus can load the image file. For example, the format of the image file can be DICOM. The information of the region of interest, the interpretation text (comment information) corresponding to the region of interest, and the information of the display region to display the interpretation text (comment information) are included in the DICOM image file. The comment information and the information of the display region are held as data corresponding to, for example, Annotation of GSPS defined by DICOM. GSPS is short for Grayscale Softcopy Presentation State. The information of a slice image to display the above-described interpretation text (comment information) display region is also included in the DICOM image file.

The character string display region of the interpretation text may be moved in accordance with an operation input of the user. For example, assume that an operation input to move the character string display region (first display region) to a position to overlap the related region (second display region) of the region of interest is done. In this case, the display position of at least one of the first display region and the second display region is determined not to make the first display region and the second display region overlap each other. This can prevent the character string display region of the interpretation text from overlapping the related region before and after the movement of the character string display region of the interpretation text and clearly display the correspondence between the medical image and the interpretation text.

In the above-described embodiment, as the keyword to be extracted from the interpretation text in step S203, a character string representing anatomical information such as an organ name to be displayed in the medical image is set in advance. However, the keyword set in advance is not limited to this. For example, a disease name such as nodule, cancer, pneumonia, emphysema, or mycobacteriosis may be set.

Figure 7A:
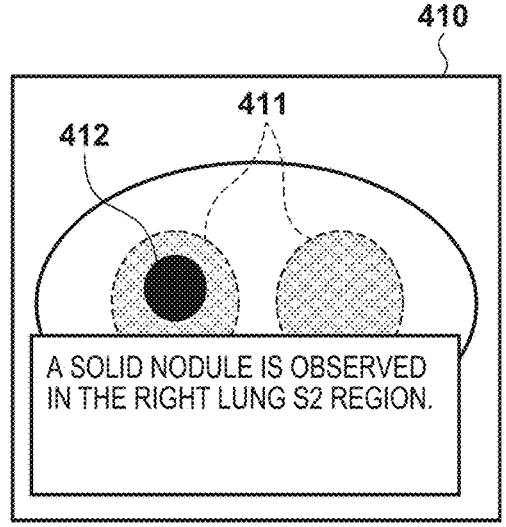
FIGS. 7A and 7B are views showing examples in which a character string display region is overlay-displayed on a medical image.

The character string display region display position determination method in a case in which "nodule" is set as the keyword will be described here with reference to FIG. 7A. The medical image 410, the broken lines 411, and the black circle 412 in FIG. 7A are the same as those shown in FIG. 4.

In step S202, "a solid nodule is observed in the right lung S2 region" is acquired as an interpretation text. In step S203, since "nodule" is set as the keyword, "nodule" is extracted from the interpretation text. In step S204, the region of "nodule" is acquired from the medical image. The extraction of the region of the nodule is performed by region segmentation processing such as graph cut processing.

In step S205, the display position determination conditions are set to "the entire character string display region is located inside the medical image" and "the character string display region does not overlap the inside of the region extracted based on the keyword of the interpretation text" as in the above-described embodiment. In this case, the display position of the character string display region is determined to a region inside the medical image 410 and outside the black circle 412. According to the display position determination conditions, the display position can be located either inside or outside the broken lines 411, unlike the above-described embodiment. In FIG. 7A, the display position of the character string display region is located inside the medical image 410 and outside the black circle 412. Hence, the display position of the character string display region shown in FIG. 7A is an appropriate display position that meets the conditions.

Figure 7B:
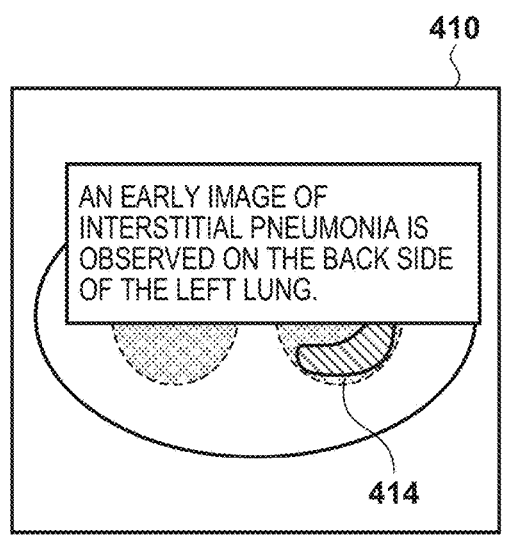

Another example in which "pneumonia" is set as the keyword will be described with reference to FIG. 7B. A hatched region 414 in FIG. 7B indicates a region where a pneumonic image is extracted in the medical image. In step S202, "an early image of interstitial pneumonia is observed on the back side of the left lung" is acquired as an interpretation text. In step S203, since "pneumonia" is set as the keyword, "pneumonia" is extracted from the interpretation text. In step S204, the region of "pneumonia" is acquired from the medical image. The region of the pneumonia is extracted by, for example, storing a texture pattern representing pneumonia in advance and extracting a region having the texture pattern in the medical image. Extraction processing of a disease region having a specific pattern in an organ can also be executed by a known method. In step S205, the display position determination conditions are set to "the entire character string display region is located inside the medical image" and "the character string display region does not overlap the inside of the region extracted based on the keyword of the interpretation text" as in the above-described embodiment. In this case, the display position of the character string display region is determined to a region inside the medical image 410 and outside the hatched region 414. In FIG. 7B, the display position of the character string display region is located inside the medical image 410 and outside the hatched region 414. Hence, the display position of the character string display region shown in FIG. 7B is an appropriate display position that meets the conditions.

As described above, when the interpretation text is displayed not to overlap the region with the disease based on the keyword such as a disease name, the correspondence between the interpretation text and the region of interest of the medical image can more easily be grasped. Note that the above-described keywords set in advance are merely examples and are not limited to the examples.

Figure 8:
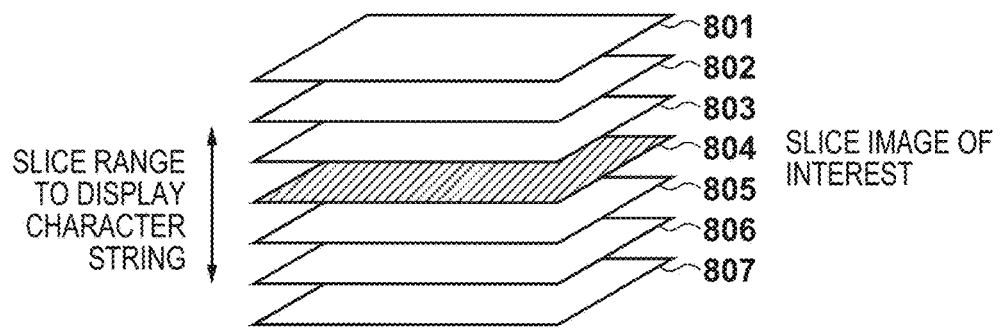
FIG. 8 is a view schematically showing slice images and a range to display a character string.

In the above-described embodiment, the display position of the character string display region is determined only for a slice image of interest in step S205. However, the display position may be determined even on an image at another slice position. A case in which the display position of the character string display region is determined even on an image at another slice position will be described with reference to FIG. 8. Referring to FIG. 8, reference numerals 801 to 807 denote medical images at slice positions, and the image 804 is the slice image of interest.

FIG. 8 shows an example in which the display position of the character string display region is determined on medical images at slice positions within a predetermined range from the slice position of the slice image of interest. The predetermined range may be determined using a fixed value to, for example, "two slice positions on each of the front and back sides of the slice position of the slice image of interest". In this case, the display position of the character string display region is determined on the medical images at the slice positions 802 to 806 in FIG. 8. As another example, the range of slice positions to determine the display position of the character string display region may be set based on the size of the region extracted in step S204. More specifically, if the size of the extracted region is small, a narrow range is set. If the size of the extracted region is large, a wide range is set. Alternatively, the user may manually set the range.

The display position of the character string display region at another slice position may be determined using the same display position determination conditions as those used to determine the display position of the character string display region on the slice image of interest. The display position of the character string display region at each slice position may be the same as that on the slice image of interest. In such a case, depending on the slice position, the character string display region may be displayed inside the region extracted in step S204 so the display position determination conditions are not met. In this case, the display position determination conditions are set to "the entire character string display region is located inside the medical image", "the character string display region does not overlap the inside of the region extracted based on the keyword of the interpretation text", and "the display positions are the same for all slice positions". Accordingly, the display position of the character string display region does not change between the slice positions, and the region of the medical image closely related to the contents of the interpretation text can be avoided from being set to the display position.

As described above, when the medical image to be displayed includes a plurality of slice images acquired from the same object, the display position determination unit 45 determines the slice image to display the character string display region including the interpretation text from the plurality of slice images. The display processing unit 46 then displays the character string display region including the interpretation text on the determined slice image. Hence, according to this embodiment, since the character string displayed on the medical image is displayed at the plurality of slice positions, the user can more easily recognize the character string.

In this embodiment, the display processing unit 46 displays the interpretation text associated with the region of interest together with each slice image existing within a predetermined distance from the region of interest in a direction perpendicular to the cross section of the slice image. For this reason, even if a disease is distributed three-dimensionally, the user can easily grasp the correspondence between the interpretation text and the region with the disease.

In the above-described embodiment, a position indicating specific coordinates in the medical image is recorded and used as the position-of-interest information of the interpretation report. However, the position-of-interest information is not limited to this. For example, the user may set the position of interest as a range (to be referred to as a range of interest hereinafter). More specifically, an ROI (Region Of Interest) or VOI (Volume Of Interest) is set.

Figure 9A:
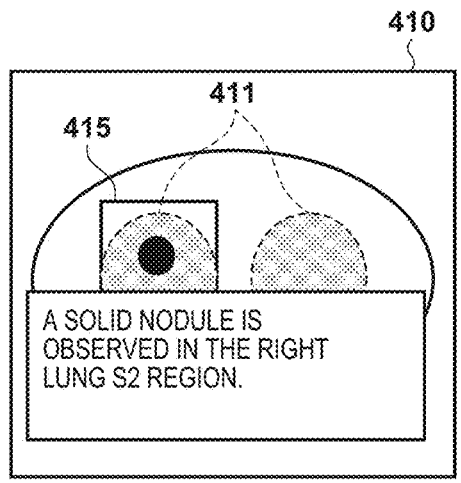
FIGS. 9A, 9B, and 9C are views showing examples in which a character string display region is overlay-displayed on a medical image.
Figure 9B:
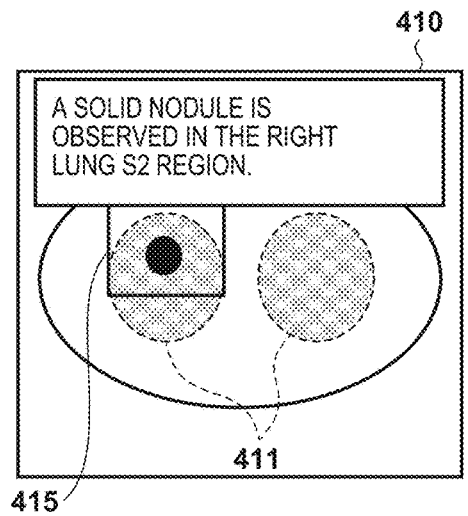
Figure 9C:
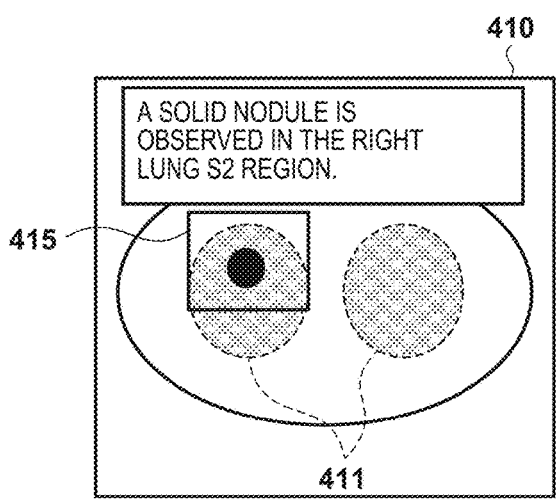

An example in which an ROI is set will be described with reference to FIGS. 9A, 9B, and 9C. The medical image 410 and the broken lines 411 in FIGS. 9A, 9B, and 9C are the same as those shown in FIG. 4. A range of interest corresponding to the interpretation text of the medical image is set as an ROI 415 by the user. The character string display region display position determination method in this case will be described.

The processes of steps S201 to S204 are the same as in the above-described embodiment. In FIG. 9A, the display position determination conditions in step S205 are set to "the entire character string display region is located inside the medical image" and "the character string display region does not overlap the inside of the position-of-interest region". In this case, the display position of the character string display region is determined to a region inside the medical image 410 and outside the ROI 415. The display position can be located either inside or outside the broken lines 411, unlike the above-described embodiment. In FIG. 9A, the display position of the character string display region is located inside the medical image 410 and outside the ROI 415. Hence, the display position of the character string display region shown in FIG. 9A is an appropriate display position that meets the conditions. Note that if the conditions set in advance in step S205 do not use the information of an anatomical region in the medical image, as in FIG. 9A, the processes of steps S203 and S204 can be omitted.

As another example, the display position determination conditions in step S205 are set as follows. That is, the display position determination conditions are set to "the entire character string display region is located inside the medical image", "the character string display region does not overlap the inside of the region extracted based on the keyword of the interpretation text", and "the character string display region does not overlap the inside of the position-of-interest region". In this case, the display position of the character string display region 420 is determined to a region inside the medical image 410, outside the broken lines 411, and outside the ROI 415. In FIG. 9B, the display position of the character string display region is located inside the medical image 410, outside the broken lines 411, and outside the ROI 415. Hence, the display position of the character string display region shown in FIG. 9B is an appropriate display position that meets the conditions. According to the above conditions, the edge of the character string display region and the edge of the ROI may continue, and the ROI may be hard to see. In this case, the display position determination conditions are set as follows. That is, display position determination conditions are set to the entire character string display region is located inside the medical image", the character string display region does not overlap the inside of the region extracted based on the keyword of the interpretation text", and "the character string display region is located outside the position-of-interest region at a predetermined distance". The predetermined distance may be determined in advance or set by the user. In FIG. 9C, the display position of the character string display region is located inside the medical image 410, outside the broken lines 411, and outside the ROI 415 at a predetermined distance. Hence, the display position of the character string display region shown in FIG. 9C is an appropriate display position that meets the conditions.

Figure 10A:
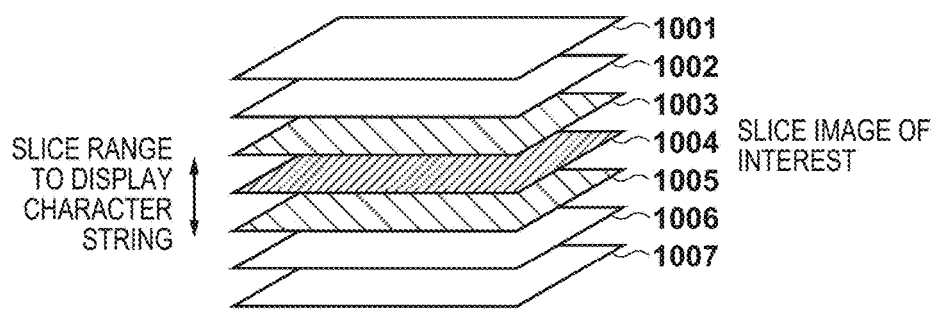
FIGS. 10A and 10B are views schematically showing slice images and a range to display a character string.
Figure 10B:
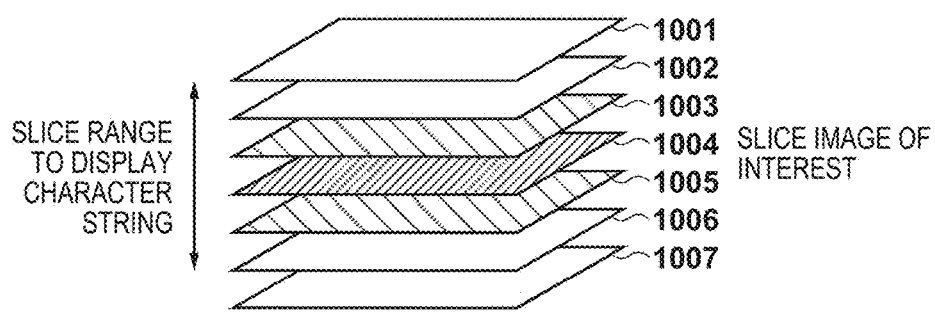

When the user sets, not an ROI, but a VOI, as the range of interest, the display position of the character string display region can be determined in the slice image of interest by the same processing as that for the ROI. When determining the display position of the character string display region at a plurality of slice positions within a predetermined range, as in the above-described embodiment, slice positions where the VOI is set may be set as the range. A case in which the display position is determined at a plurality of slice positions will be described with reference to FIGS. 10A and 10B. Referring to FIGS. 10A and 10B, reference numerals 1001 to 1007 denote medical images at slice positions, and the image 1004 is the slice image of interest. An example in which a VOI is set on the medical images at the slice positions 1003 to 1005 will be described. In this case, the slice positions 1003 to 1005 are set to the range. As another example, a range from a slice position a little before the slice positions where the VOI is set to a slice position a little after the slice positions may be set as the range to display the character string display region. FIG. 10B shows an example in which the range is set from the second preceding slice position to one slice position after the slice positions where the VOI is set. In this case, the slice positions 1001 to 1006 are set to the range.

FIG. 16 is a view showing a detailed display example of the image display region 310 shown in FIG. 3. In FIG. 16, the display position of the character string display region is determined by the method described with reference to FIG. 9C.

Referring to FIG. 16, the image display region 310 includes the following partial regions. A test list 1601 is a region to display, in a list format, all tests (current and past tests) of a patient as a current test target. A thumbnail list 1602 is a region to display, in a thumbnail list format, all images included in a test selected by the user from the test list displayed in the test list 1601. Each image included in the test may be one slice image or a series image (3D image) formed from a plurality of slice images. A thumbnail is normally an image created by reducing one slice image. To create a thumbnail from a series image, a representative image (for example, a slice image whose slice position is located at the center) in the series image is reduced.

A tool bar 1603 is a region to arrange and display a plurality of buttons (icons). When the user selects a button on the tool bar 1603, a function (for example, image display form change, graphic drawing, or character string display region drawing) associated with the button in advance is executed. An image/finding display tile 1604 is a region to display an image display tile 1605 (to be described later), a finding list 1606, and a diagnosis support information list (CAD list) 1607.

One to a predetermined upper limit number of image/finding display tiles 1604 can be displayed in accordance with a user instruction. FIG. 16 shows an example in which four image/finding display tiles 1604 are displayed in a 2×2 layout pattern. The image display tile 1605 is a region to display an image corresponding to a thumbnail selected by the user. The image displayed in the image display tile 1605 can undergo an operation such as change of the displayed slice position, image translation/enlargement/rotation, or intensity value conversion in accordance with a user instruction. In addition, graphic drawing on the image displayed in the image display tile 1605 or graphic deletion can be performed in accordance with a user instruction. In the example shown in FIG. 16, the user draws an elliptical pattern surrounding the region of interest (ROI) of the image using the operation unit 35 such as a mouse. The character string display region is displayed using the method described with reference to FIG. 9C. The user can input or edit an arbitrary character string (to be referred to as a finding hereinafter) in the character string display region using the operation unit 35 such as a keyboard.

The finding list 1606 is a region to display, in a list format, all findings arranged on the image (for a series image, a plurality of slice images) displayed in the image display tile 1605. When the user selects an arbitrary finding displayed in the finding list 1606, a slice image with the selected finding being arranged is displayed in the image display tile 1605. The CAD list 1607 is a region to display, in a list format, all pieces of diagnosis support information obtained by a diagnosis support information acquisition unit (not shown) provided in the control unit 37. The diagnosis support information can also be acquired for an ROI designated by the user, or acquired by an ROI detection device (not shown) provided in the control unit 37. When the user selects arbitrary diagnosis support information displayed in the CAD list 1607, a slice image existing in an ROI corresponding to the selected diagnosis support information is displayed in the image display tile 1605.

As described above, in this embodiment, since the display position of the character string display region of the interpretation text is determined based on an ROI or VOI, the user can easily grasp the correspondence between the interpretation text and the region of interest in the medical image.

In the above-described embodiment, the display position of the character string display region is determined from the medical image and the interpretation report corresponding to it. However, the display position of the character string display region may be determined from medical images of a plurality of time points and interpretation reports corresponding to them. For example, past medical images or interpretation reports of the same patient may be used.

Figure 11:
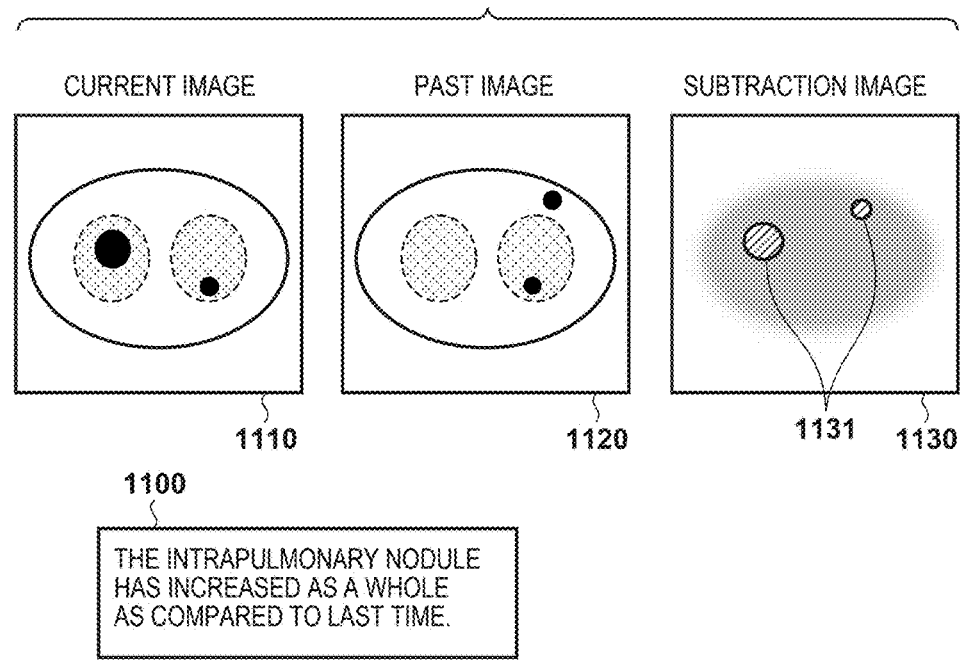
FIG. 11 is a view for explaining a current image, a past image, and a subtraction image.
Figure 12:
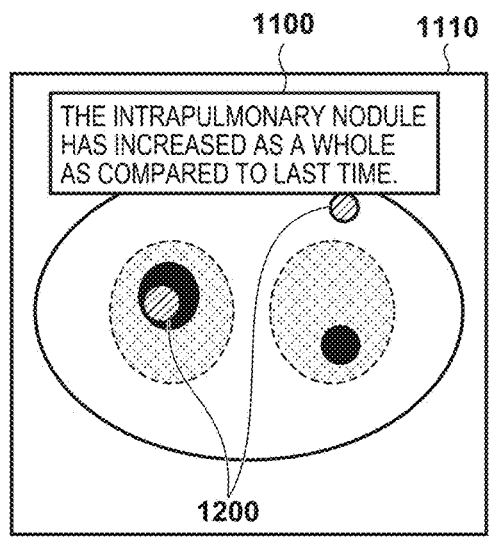
FIG. 12 is a view showing an example in which a character string display region is overlay-displayed on a medical image.

A case in which the display position of the character string display region is determined from medical images or interpretation reports of a plurality of time points will be described with reference to FIGS. 11 and 12. Referring to FIG. 11, a medical image (current image) 1110 is a medical image corresponding to an interpretation text written by the user and displayed in a character string display region 1100. A medical image (past image) 1120 is an image of the same patient captured at a time point before the capturing time of the medical image 1110. A subtraction image 1130 is the subtraction image between the medical image 1110 and the medical image 1120. The subtraction image can be generated by, for example, performing deformation alignment between the medical image 1110 and the medical image 1120 using deformation alignment processing such as FFD (Free-Form Deformation) and subtraction processing between the images. Hatched regions 1131 on the subtraction image 1130 are regions each having a subtraction between the current image 1110 and the past image 1120. Hatched regions 1200 shown in FIG. 12 indicate positions on the current image 1110 corresponding to the hatched regions 1131 on the subtraction image 1130.

In step S201, the current medical image 1110 is read out. In step S202, an interpretation report created for the medical image 1110 is read out. An example in which an interpretation text in the created interpretation report is "the intrapulmonary nodule has increased as a whole as compared to last time", which is displayed in the character string display region 1100 shown in FIG. 11, will be described. In step S203, "compared to last time", "relative to before", "in comparison with before" are set in advance as keywords to be extracted from the interpretation text. In this case, since "compared to last time" is set as a keyword, "compared to last time" is extracted from the interpretation text. Note that the above-described keywords set in advance are merely examples and are not limited to the examples if they are character strings assumed to be created over time by the user in interpretation texts compared to past medical images.

In step S204, the past image 1120 is read out, and the subtraction image 1130 is generated using the above-described method. A region (for example, the hatched region 1131) on the subtraction image having a subtraction value not less than a predetermined threshold is acquired. The threshold of the subtraction value may be set in advance, or the user may set an arbitrary value. In step S205, the display position determination conditions are set to "the entire character string display region is located inside the medical image" and "the character string display region does not overlap the inside of the region extracted based on the keyword of the interpretation text". In this case, the display position of the character string display region is determined to a region inside the medical image 1110 and outside the hatched regions 1200 on the current image 1110 corresponding to the positions of the hatched regions 1131 on the subtraction image. In FIG. 12, the display position of the character string display region is located inside the medical image 1110 and outside the hatched regions 1200. Hence, the display position of the character string display region 1100 shown in FIG. 12 is an appropriate display position that meets the conditions.

As described above, in this embodiment, the subtraction image between a medical image and another medical image is acquired, and the display position of the character string display region of the interpretation text is determined based on the pixel values of the subtraction image. Hence, a region important for diagnosis such as a portion where a disease extends is displayed while presenting the correspondence with the interpretation text, thereby prompting the doctor to make a diagnosis.

In the above-described embodiment, an example in which the character string display region is a region having a predetermined size and shape in step S205 has been described. However, the size or shape of the character string display region may be changeable as needed depending on the display position of the character string display region, the amount of the character string to be displayed, the medical image to be overlay-displayed, the extracted region, and the like.

This will be described with reference to FIGS. 13A, 13B, and 13C. In step S201, a medical image 1300 is read out. In step S202, an interpretation report created for the medical image 1300 is read out. An example in which an interpretation text in the created interpretation report is "a solid nodules is observed in the right lung S2 region. The nodule has an irregular shape and includes spicula, and a lung cancer is suspected first of all", which is displayed in a character string display region 1302 shown in FIG. 13A, will be described. In step S203, "lung" is extracted from the interpretation text as a keyword. In step S204, a lung region 1301 corresponding to the keyword is extracted from the medical image 1300. In step S205, the display position determination conditions are set to "the entire character string display region is located inside the medical image" and "the character string display region does not overlap the inside of the region extracted based on the keyword of the interpretation text", as in the above-described embodiment.

Figure 13A:
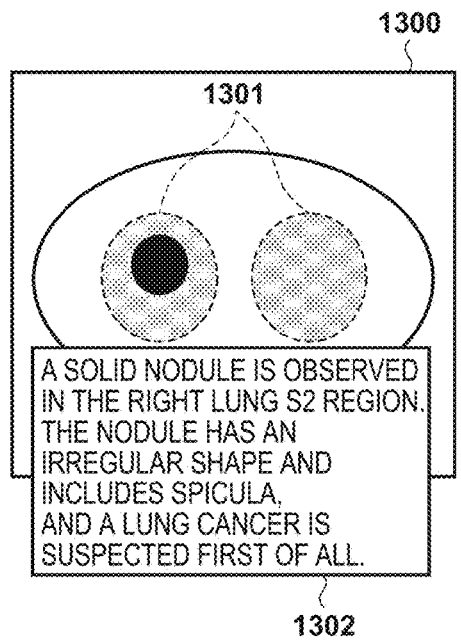
FIGS. 13A, 13B, and 13C are views showing examples in which a character string display region is overlay-displayed on a medical image.
Figure 13B:
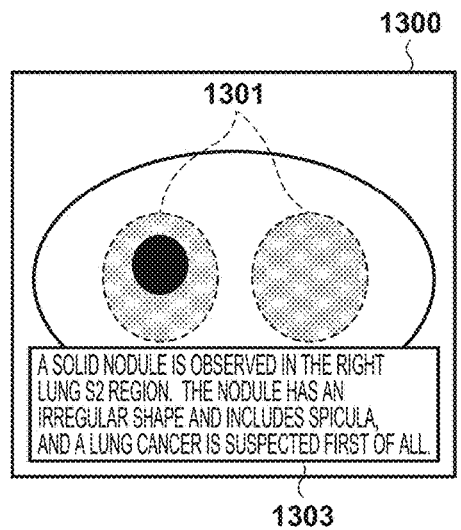
Figure 13C:
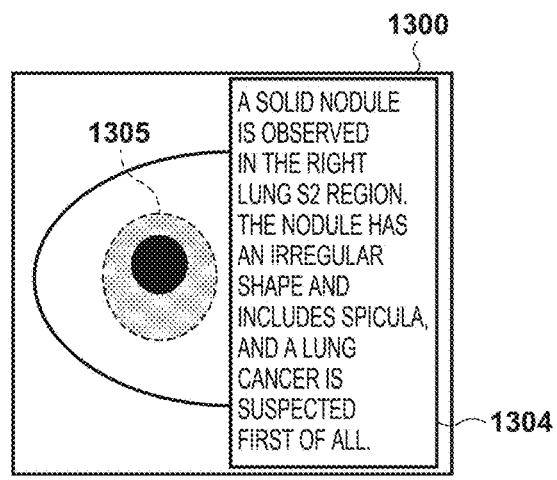

FIG. 13A shows an example in which since the character string display region 1302 is large, a position that meets the display position determination conditions does not exist in the medical image, and the character string display region cannot be fitted in the medical image. In this case, the user may be warned of the absence of a region capable of displaying the character string display region. Alternatively, as indicated by a character string display region 1303 shown in FIG. 13B, the size of the character string display region may be reduced to such a size that allows the position meeting the display position determination conditions to exist in the medical image. In FIG. 13B, the font size of the interpretation text displayed in the character string display region is reduced, thereby displaying the character string display region 1303 at a position meeting the display position determination conditions without changing the contents of the interpretation text.

As another example, an example shown in FIG. 13C will be described. In this case, in step S203, "right lung" is extracted from the interpretation text as a keyword. In step S204, a right lung region 1305 is extracted. In step S205, the display position determination conditions are set to "the entire character string display region is located inside the medical image" and "the character string display region does not overlap the inside of the region extracted based on the keyword of the interpretation text", as in the above-described embodiment. In this example, a character string display region 1304 shown in FIG. 13C is displayed at a position meeting the display position determination conditions by changing its shape, as compared to the character string display region 1302 shown in FIG. 13A.

According to this embodiment, the size or shape of the character string display region is changed based on the distribution of the related region included in the medical image, thereby displaying the character string display region on the medical image. It is therefore possible to show the correspondence between the interpretation text and the region of interest independently of the amount or size of the interpretation text.

In the above-described embodiment, one region on the medical image corresponding to one keyword extracted in step S203 is acquired in step S204 and used as a display position determination condition in step S205. However, a plurality of regions on the medical image may be acquired in correspondence with one keyword and used as display position determination conditions.

Figures 14, 15:
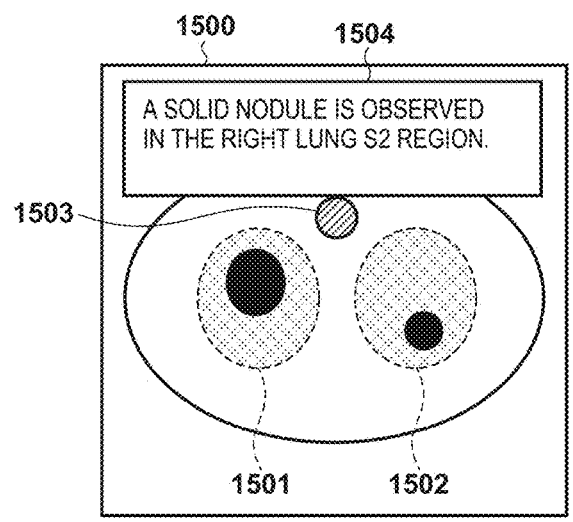
FIG. 14 is a view showing the relationship between a keyword and an acquired region.
FIG. 15 is a view showing an example in which a character string display region is overlay-displayed on a medical image.

This will be determined with reference to FIGS. 14 and 15. FIG. 14 is a view showing an example of table information representing the relationship between a preset keyword extracted from an interpretation text in step S203 and a region acquired in correspondence with the keyword in step S204. For example, referring to FIG. 14, if "brain" is extracted from an interpretation text as a keyword in step S203, a "cerebrum" region and a "cerebellum" region are acquired in step S204. As another example, if "lung" is extracted from an interpretation text as a keyword in step S203, "right lung field", "left lung field", and "bronchus" regions are acquired in step S204. In the table information, a character string associated with a region of interest in a medical image of an object and a character string representing the type of an anatomical region are thus associated with each other.

FIG. 15 shows an example in which a character string display region is displayed in a medical image when "lung" is extracted in step S203, and "right lung field", "left lung field", and "bronchus" regions are acquired in step S204. More specifically, in step S201, a medical image 1500 is read out. In step S202, an interpretation report created for the medical image 1500 is read out. An example in which an interpretation text in the created interpretation report is "a solid nodule is observed in the right lung S2 region", which is displayed in a character string display region 1504 shown in FIG. 15, will be described.

In step S203, "lung" is extracted from the interpretation text as a keyword. In step S204, a right lung region 1501, a left lung region 1502, and a bronchus region 1503 corresponding to the keyword are extracted from the medical image 1500 with reference to FIG. 12. In step S205, the display position determination conditions are set to "the entire character string display region is located inside the medical image" and "the character string display region does not overlap the inside of the region extracted based on the keyword of the interpretation text", as in the above-described embodiment. In this case, the display position of the character string display region 1504 is determined to a region inside the medical image 1500, outside the right lung region 1501, outside the left lung region 1502, and outside the bronchus region 1503. In FIG. 15, the display position of the character string display region is located inside the medical image 1500 and outside the right lung region 1501, the left lung region 1502, and the bronchus region 1503. Hence, the display position of the character string display region 1504 shown in FIG. 15 is an appropriate display position that meets the conditions.

In this embodiment, the display position of the character string display region is determined in consideration of another region that is anatomically or medically closely related to the region corresponding to the keyword in the interpretation text as well. Hence, the user can more easily recognize the character string.

Note that the interpretation report may include a plurality of regions of interest in a medical image and a plurality of interpretation texts (comment information) associated with the regions of interest, and the display position determination unit 45 may determine, for the plurality of interpretation texts, the display positions of character string display regions that do not overlap each other. This enables simultaneous display of the plurality of regions of interest and the corresponding interpretation texts (comment information) on one medical image without overlap.

In the above-described embodiment, in step S206, the display processing unit 46 displays, on the display unit 36, the character string overlaid on the medical image. However, a medical image in which the character string is directly embedded may be created and displayed.

The processes of steps S201 to S205 are the same as in the above-described embodiment. In step S206, a second medical image is created, in which some or all of the character strings of the interpretation text acquired in step S202 are embedded at the display position determined in step S205 on the medical image read out in step S201. The second medical image is displayed on the display unit 36.

As described above, in this embodiment, a new medical image with the interpretation text arranged at the display position of the character string display region is generated. The new medical image is displayed on the display unit 36 as a medical image including the interpretation text. It is therefore possible to show the correspondence between the medical image and the interpretation text without making the interpretation text overlay the related region as in a case in which the character string is overlaid on the medical image.

In the above-described embodiment, each unit of the medical image display apparatus 10 is implemented by software in the local environment. However, a server-client system may be formed in which at least some of the functions of the control unit 37 in the medical image display apparatus 10 are executed by a server using a LAN.

For example, the processes of the medical image acquisition unit 41, the interpretation report acquisition unit 42, the keyword extraction unit 43, the region acquisition unit 44, and the display position determination unit 45 which are expected to have large calculation amounts are implemented by the server. The process of the display processing unit 46 that performs processing of finally displaying a medical image to the user may be implemented on the client side. More specifically, when a case number is selected from a list (not shown) on the client side, the selected case number is transmitted to the server via the LAN. On the server side, a medical image and an interpretation report are acquired based on the selected case number, and the above-described processing is performed to finally determine the display position of the interpretation text (steps S201 to S205). Next, the server transmits the medical image, the interpretation report, the interpretation text, and the display position of the interpretation text to the client side. On the client side, the medical image and the interpretation text are displayed based on the transmitted contents (step S206).

According to this embodiment, even if the calculation resource on the client side is small, the correspondence between the medical image and the interpretation text can clearly be displayed using the server.

As described above, in each embodiment of the present invention, a position of interest or a range of interest on a medical image and an interpretation text (comment information) for the position of interest or the range of interest are acquired. The display position of the comment information (a character string or the like) on the medical image is determined based on the contents of the character string. It is therefore possible to determine the display position when displaying the character string on the medical image based on the contents of the character string and overlay-display the character string at the display position on the medical image. The character string can thus be avoided from being overlaid at an anatomically important position on the medical image or at a position on the medical image related to the contents of the character string. It is therefore possible to provide a medical image display technique of performing display without hindering the user from confirming the contents of the character string.

According to the present invention, the user can more easily grasp the correspondence between a medical image and an interpretation report.

Other Embodiments

Embodiment(s) of the present invention can also be realized by a computer of a system or an apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., an application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), or a micro processing unit (MPU)) and may include a network of separate computers or separate processors to read out and to execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or a Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-177914, filed on Sep. 9, 2015, and Japanese Patent Application No. 2016-080480, filed on Apr. 13, 2016, which are hereby incorporated by reference herein in their entirety.

What is claimed is:

1. An information processing apparatus comprising:
a report acquisition unit adapted to acquire report information including a region of interest in a medical image and comment information associated with the region of interest;
a related region acquisition unit adapted to acquire a region related to the region of interest in the medical image;
a determination unit adapted to determine a display position of a display region of the comment information so as not to make the display region of the comment information overlap the related region; and
a display control unit adapted to display the medical image including the comment information so that the comment information is displayed at the determined display position of the display region on a display unit.

2. The apparatus according to claim 1, wherein the determination unit changes the display position of the display region according to a modification of the comment information, and
the display control unit displays the medical image including the comment information at the changed display position of the display region.

3. The apparatus according to claim 1, wherein the related region acquisition unit acquires an anatomical region including the region of interest as the related region, the anatomical region being a partial region of a region that a patient occupies in the medical image.

4. The apparatus according to claim 3, wherein the related region acquisition unit further acquires another anatomical region related to the anatomical region as the related region.

5. The apparatus according to claim 3, wherein the related region acquisition unit acquires the anatomical region as the related region based on the comment information.

6. The apparatus according to claim 5, wherein the related region acquisition unit extracts a keyword from a character string included in the comment information, and acquires the anatomical region based on the keyword.

7. The apparatus according to claim 6, wherein the related region acquisition unit acquires the anatomical region as the related region based on table information in which a character string associated with the region of interest and a type of the anatomical region are associated with each other.

8. The apparatus according to claim 6, wherein according to extraction of the keyword from the character string included in the comment information by the related region acquisition unit, the display control unit displays a portion corresponding to the keyword so as to be distinguished from another character string.

9. The apparatus according to claim 6, wherein the related region acquisition unit extracts an organ name and/or a disease name as the keyword.

10. The apparatus according to claim 3, wherein the related region acquisition unit acquires the anatomical region based on a position of the region of interest in the medical image.

11. The apparatus according to claim 10, wherein if the anatomical region cannot be acquired based on a character string included in the comment information, the related region acquisition unit acquires the anatomical region based on the position of the region of interest in the medical image.

12. The apparatus according to claim 1, wherein the medical image to be displayed includes a plurality of slice images acquired from the same patient, the determination unit further determines a slice image to be displayed together with the comment information from the plurality of slice images, and
the display control unit displays the comment information in the display region of the determined slice image.

13. The apparatus according to claim 1, wherein the medical image to be displayed includes a plurality of slice images acquired from the same patient, and
the display control unit displays comment information associated with the region of interest together with each slice image existing within a predetermined distance from the region of interest in a direction perpendicular to a cross section of the slice image.

14. The apparatus according to claim 1, further comprising an image acquisition unit adapted to acquire a subtraction image between the medical image and another medical image,
wherein the determination unit determines the display position of the display region based on pixel values of the subtraction image.

15. The apparatus according to claim 1, wherein the determination unit determines the display position of the display region such that the display position is included in a region occupied by the medical image.

16. The apparatus according to claim 1, further comprising a generation unit adapted to generate a new medical image with the comment information arranged in the display region displayed at the display position determined by the determination unit,
wherein the display control unit displays the new medical image as a medical image including the comment information.

17. The apparatus according to claim 1, further comprising a creation unit adapted to create an image file of the medical image including the comment information and region information representing the display region determined by the determination unit.

18. The apparatus according to claim 1, wherein the report information includes a plurality of regions of interest in the medical image and a plurality of pieces of comment information associated with the regions of interest, and
the determination unit determines, for display regions of the plurality of pieces of comment information, display positions that do not overlap each other.

19. The apparatus according to claim 1, further comprising a moving unit adapted to move the display region of the comment information in accordance with an operation input of a user,
wherein if an operation input to move a first display region to a position to overlap a second display region is done, the determination unit determines the display position of at least one of the first display region and the second display region not to make the first display region and the second display region overlap each other.

20. The apparatus according to claim 1, wherein the related region is the region of interest.

21. An information processing apparatus comprising:
a report acquisition unit adapted to acquire report information including a region of interest in a medical image and comment information associated with the region of interest;
a related region acquisition unit adapted to acquire a related region in the medical image based on a character string included in the comment information;
a determination unit adapted to determine a display position of a display region of the comment information so as not to make the display region of the comment information overlap the related region; and a display control unit adapted to display the medical image including the comment information so that the comment information is displayed at the determined display position of the display region on a display unit.

22. An information processing method comprising:

acquiring, by a report acquisition unit, report information including a region of interest in a medical image and comment information associated with the region of interest;

acquiring, by a related region acquisition unit, a region related to the region of interest in the medical image;

determining, by a determination unit, a display position of a display region of the comment information so as not to make the display region of the comment information overlap the related region; and displaying, by a display control unit, the medical image including the comment information so that the comment information is displayed at the determined display position of the display region on a display unit.

23. An information processing method comprising:

acquiring, by a report acquisition unit, report information including a region of interest in a medical image and comment information associated with the region of interest;

acquiring, by a related region acquisition unit, a related region in the medical image based on a character string included in the comment information;

determining, by a determination unit, a display position of a display region of the comment information so as not to make the display region of the comment information overlap the related region; and displaying, by a display control unit, the medical image including the comment information so that the comment information is displayed at the determined display position of the display region on a display unit.

24. A non-transitory computer-readable storage medium storing a computer program for causing a computer to function as each unit of an information processing apparatus comprising:

a report acquisition unit adapted to acquire report information including a region of interest in a medical image and comment information associated with the region of interest;

a related region acquisition unit adapted to acquire a region related to the region of interest in the medical image;

a determination unit adapted to determine a display position of a display region of the comment information so as not to make the display region of the comment information overlap the related region; and a display control unit adapted to display the medical image including the comment information so that the comment information is displayed at the determined display position of the display region on a display unit.

25. An information processing apparatus comprising:

a report acquisition unit adapted to acquire comment information associated with a medical image;

a related region acquisition unit adapted to acquire a related region in the medical image based on a character string included in the comment information;

a determination unit adapted to determine a display position of a display region of the comment information so as not to make the display region of the comment information overlap the related region; and a display control unit adapted to display the medical image including the comment information so that the comment information is displayed at the determined display position of the display region on a display unit.

26. An information processing method comprising:

acquiring comment information associated with a medical image;

acquiring a related region in the medical image based on a character string included in the comment information;

determining a display position of a display region of the comment information so as not to make the display region of the comment information overlap the related region; and displaying the medical image including the comment information so that the comment information is displayed at the determined display position of the display region on a display unit.

27. A non-transitory computer-readable storage medium storing a computer program for causing a computer to function as each unit of an information processing apparatus comprising:

a report acquisition unit adapted to acquire comment information associated with a medical image;

a related region acquisition unit adapted to acquire a related region in the medical image based on a character string included in the comment information;

a determination unit adapted to determine a display position of a display region of the comment information so as not to make the display region of the comment information overlap the related region; and a display control unit adapted to display the medical image including the comment information so that the comment information is displayed at the determined display position of the display region on a display unit.

28. An information processing apparatus comprising:

a report acquisition unit adapted to acquire report information including comment information associated with a region of interest in a medical image;

a determination unit adapted to determine a display position of a display region of the comment information so as not to make the display region of the comment information overlap a region related to the region of interest in the medical image; and a display control unit adapted to display the medical image including the comment information so that the comment information is displayed at the determined display position of the display region on a display unit.

* * * * *